(12) United States Patent
Chang (10) Patent No.: US 7,637,267 B2
(45) Date of Patent: Dec. 29, 2009

(54) FLOSSING TOOL WITH TENSIONING AND ADVANCING CONTROL

(76) Inventor: Jih Chang, 6F, No, 338, Chung-Hsan. Rd., Sec 1, Yung-Ho City, Taipei County (TW) 234

( * ) Notice: Subject to any disclaimer, the term of this patent is extended or adjusted under 35 U.S.C. 154(b) by 209 days.

(21) Appl. No.: 11/498,060

(22) Filed: Aug. 3, 2006

(65) Prior Publication Data

US 2008/0041413 A1    Feb. 21, 2008

(51) Int. Cl.
*A61C 15/00* (2006.01)
(52) U.S. Cl. ..................................................... 132/323
(58) Field of Classification Search ................. 132/323, 132/324, 326, 327
See application file for complete search history.

(56) References Cited

U.S. PATENT DOCUMENTS 6,394,103 B1 *    5/2002    Forsyth, III ................. 132/323

* cited by examiner

*Primary Examiner*—Robyn Doan
*Assistant Examiner*—Rachel R Steitz
(74) *Attorney, Agent, or Firm*—Bacon & Thomas, PLLC (57) ABSTRACT

A flossing tool comprises in general a fork shape handle body, a lever and a rotor. The handle body has eyelets to direct the floss. The lever is pivoted on the neck of the handle body to stretch the floss directly or via the rotor. The rotor has one or two reels for winding the floss. The tool provides constant controllable tensioning and easy advancing operation of the floss. Four embodiments are illustrated in this invention, in the fourth embodiment a floss container is included.

2 Claims, 10 Drawing Sheets

FLOSSING TOOL WITH TENSIONING AND ADVANCING CONTROL

BACKGROUND OF THIS INVENTION

1. Field of this Invention

The present invention relates to a dental flossing tool and more particularly, it relates to a manual flossing tool with controllable tensioning and advancing mechanism.

2. Description of the Prior Art

When flossing, it is required to stretch the floss taut using sawing motion to slide through tightly adjoined teeth, then slack a little to curve it into "C" shape against the side of a tooth, then stretch it again properly but not too tight, to scrape the tooth outwardly from beneath the gum line. It is also required to shift out soiled or frayed sections replacing with fresh ones frequently during flossing. Human hands are capable of doing both, but awkward to jam into the mouth and the fingers are not comfortable when wrapped with floss strands.

Therefore an ideal tool to aid flossing, shall provide the user means to taut and slack the floss at will, and to replace the soiled sections easily. At the same time for purpose of putting the tool in practical use, ergonomic handling, positively tying down the loose end(s) of the floss, isolation of spent floss from fresh section shall also be included in consideration.

Over the years numerous tools had been devised to aid flossing, among which some have good tensioning methods and some have effective advancing means, but combination of the two in one flossing tool still have room to perfection. Combining all other functionalities together with tensioning and advancing mechanism into one flossing tool yet leaves further room for endeavors.

BRIEF SUMMARY OF THIS INVENTION

Aiming the objectives of an ideal flossing tool, the present invention comprises features as follows:

A fork shape handle body forms an elongated hollow handle on one end, a bifurcated pair of arms on the other, and on the neck near the middle a triangular mount is shaped for pivotally supporting the lever. Floss is threaded through eyelets on the arm tips spans a section for flossing. Illustrated in the first and second embodiment the floss is further guided through a larger eyelet at the root of the arms to align with the reels on a rotor thereby forms a loop. In the third and fourth embodiment the larger eyelet is served as a passage way for the lever head to reach up intervening the loop between the rotor and the arm tips.

The rotor illustrated in the first, second and third embodiment has two reels, one for hauling in spent floss and another serves as supply of fresh floss. Floss is wound in opposite circumferential directions on the reels with both ends each tied in an elastomer pressurized clamp. When stretched, floss will apply torques on both reels and the torques will cancel out each other leave the rotor stationary without unwanted rotation. Turning the rotor by hand will collect spent floss on one reel and pay out fresh floss from another. In the fourth embodiment the rotor engages a ratchet mechanism and has only one reel for collecting the spent floss.

A lever pivotally mounted on the neck of the handle body is designed for constant tensioning control. In the first and second embodiment of this invention, the lever is pressed to lift the rotor to stretch the floss in the loop between the rotor and arm tips. In the third and fourth embodiment the lever is used to directly intervene the floss loop to control tautness of the floss. Also a suitable leverage is configured on the lever so that the user can apply less force to obtain desired tension on the floss span.

On each axial end of the rotor, an elastomer ring is pressed by a screw against the knurled surface of the sidewall of a reel to form a clamp for tying down the free end of the floss. Tying down or untying the floss with the clamp can be simple and effective by sliding it in or pulling it out respectively.

The handle and lever can be held by a single hand with either manner: for cleaning upper teeth, hold the handle in the palm using index and middle fingers to control the lever; for cleaning lower teeth, hold the handle in the four fingers using the thumb or thumb base to control the lever.

The handle may be molded in a hollow fashion to reduce usage of material and to serve as a passage way for floss supply when a floss container is shaped at the end of the handle. Also on the lower side of the handle facing the lever a slot opening can be made to give way for a few more rotatable degree to the lever.

Four embodiments illustrated in this invention are sequentially altered. In the first embodiment the lever and the rotor integrate with an interlock mechanism; In the second embodiment a simpler rotor and a simpler lever are devised compare to the first embodiment; the third embodiment adopts the same rotor from the second embodiment but mounts the rotor on the handle body and uses a modified lever to stretch the floss directly; the fourth embodiment includes a floss container and uses a unidirectional rotor vis-à-vis the third embodiment.

These and other objects, features and advantages of the present invention will become more apparent from the following description and the appended claims, taken in connection with the accompanying drawings in which preferred embodiment of the present invention are shown by way of illustrative example.

DETAILED DESCRIPTION OF THIS INVENTION

Figure 1:
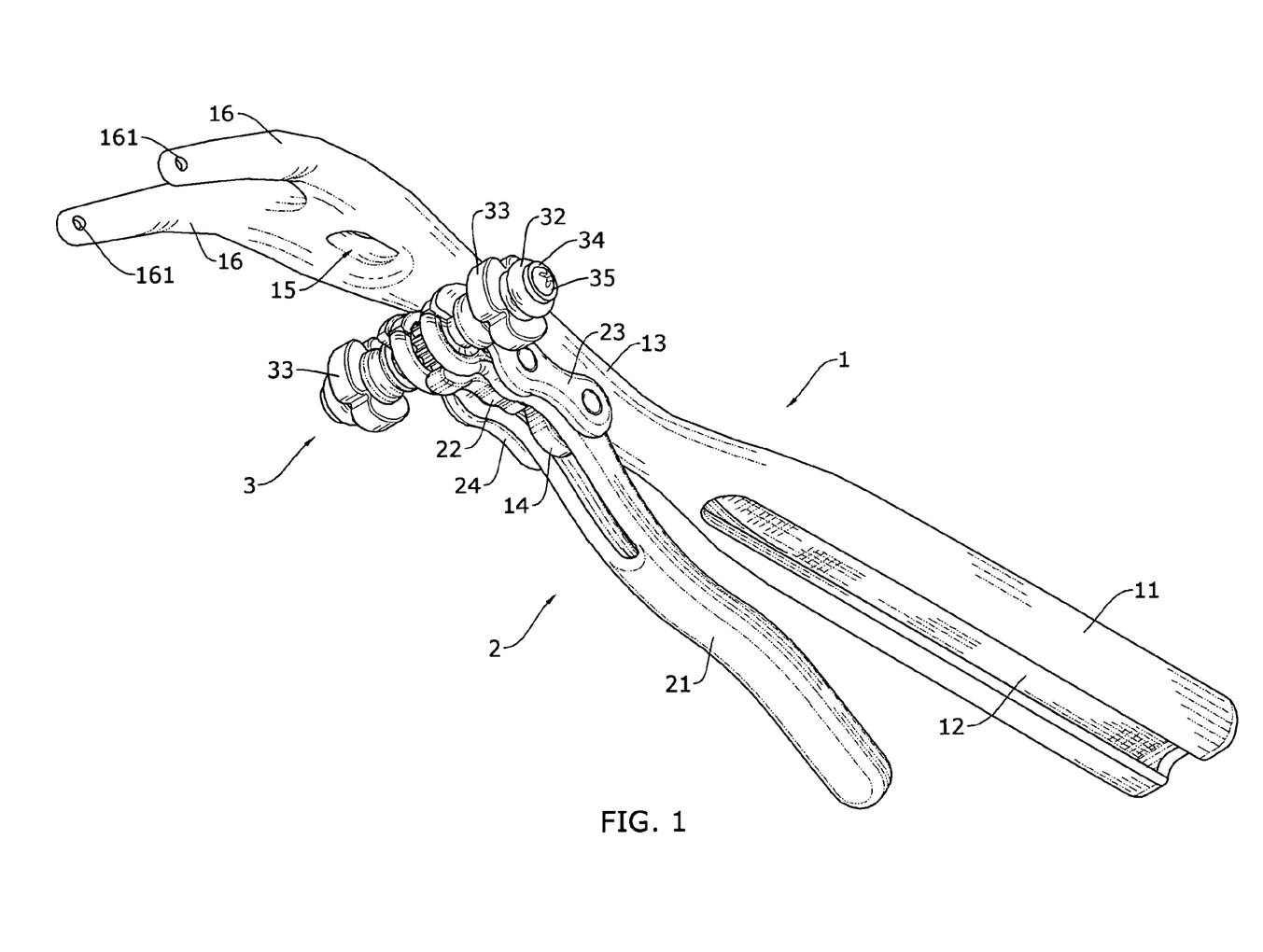
FIG. 1 is a perspective view of a flossing tool highlighting the rotor-lever interlock mechanism in the first embodiment of this invention.
Figure 3:
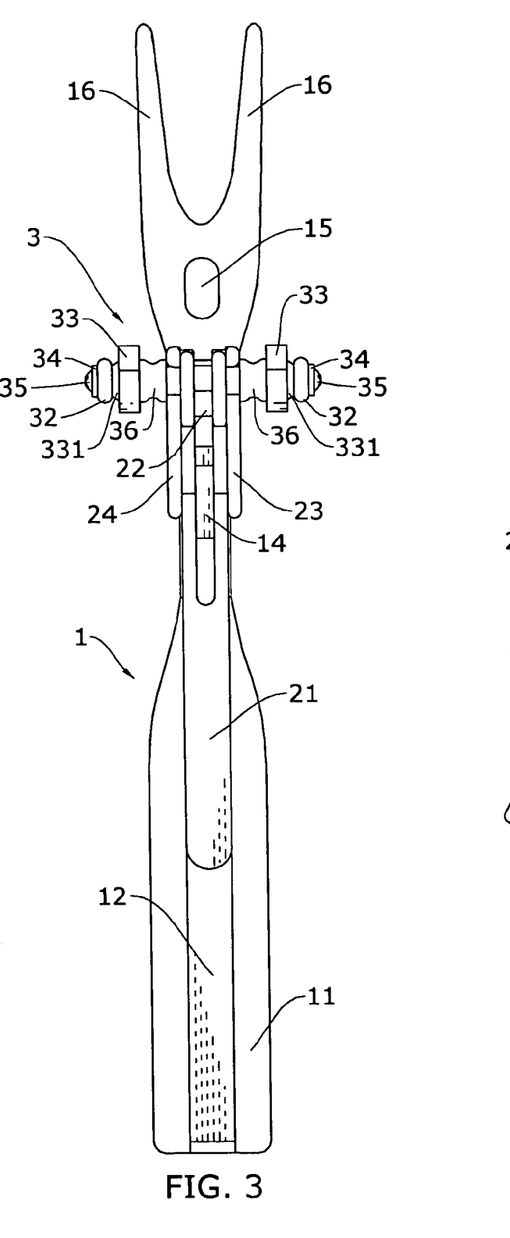
FIG. 3 is a bottom view of a flossing tool in the first embodiment of this invention.
Figure 4:
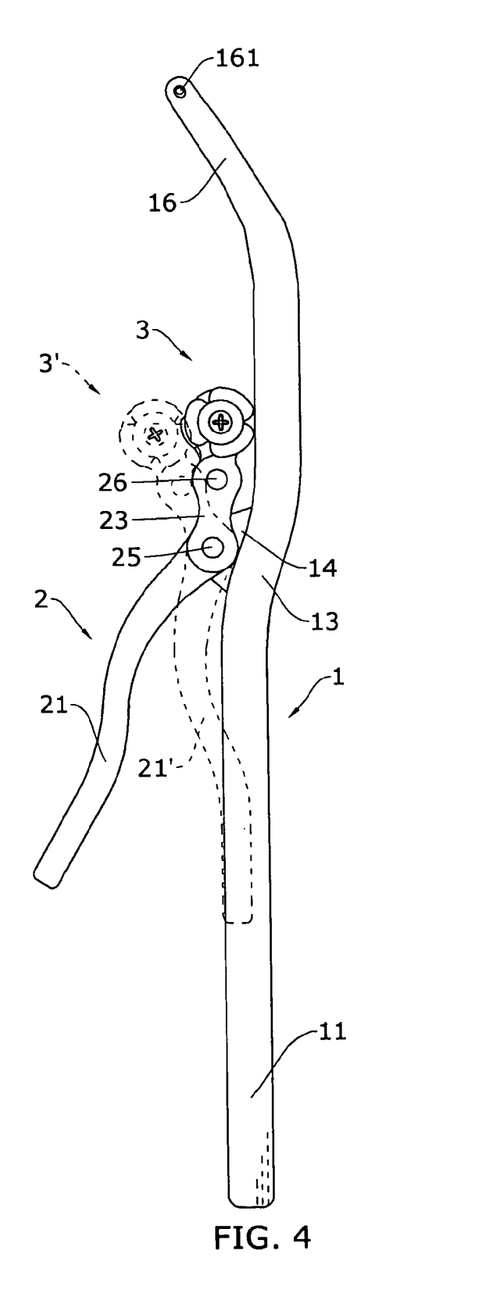
FIG. 4 is a side elevation view of a flossing tool in the first embodiment of this invention.

Referencing to FIG. 1, FIG. 3 and FIG. 4, a flossing tool in the first embodiment comprises in general a handle body 1, a lever 2, and a rotor 3. The handle body 1 forms a pair of bifurcated arms 16 on one end, an elongated hallow handle 11 on the other, and near the center at the neck 13 a triangular mount 14 is shaped for pivotally installing the lever 2. An eyelet 161 is bored on the tip of each arm 16 and a larger eyelet 15 is bored at the root of the arms. The hallow handle 11 has a slot opening 12 on the side facing the lever body 21, allowing the lever body 21 to gain a further few rotatable degrees when fully pressed indicated as 21' of FIG. 4.

Figure 2:
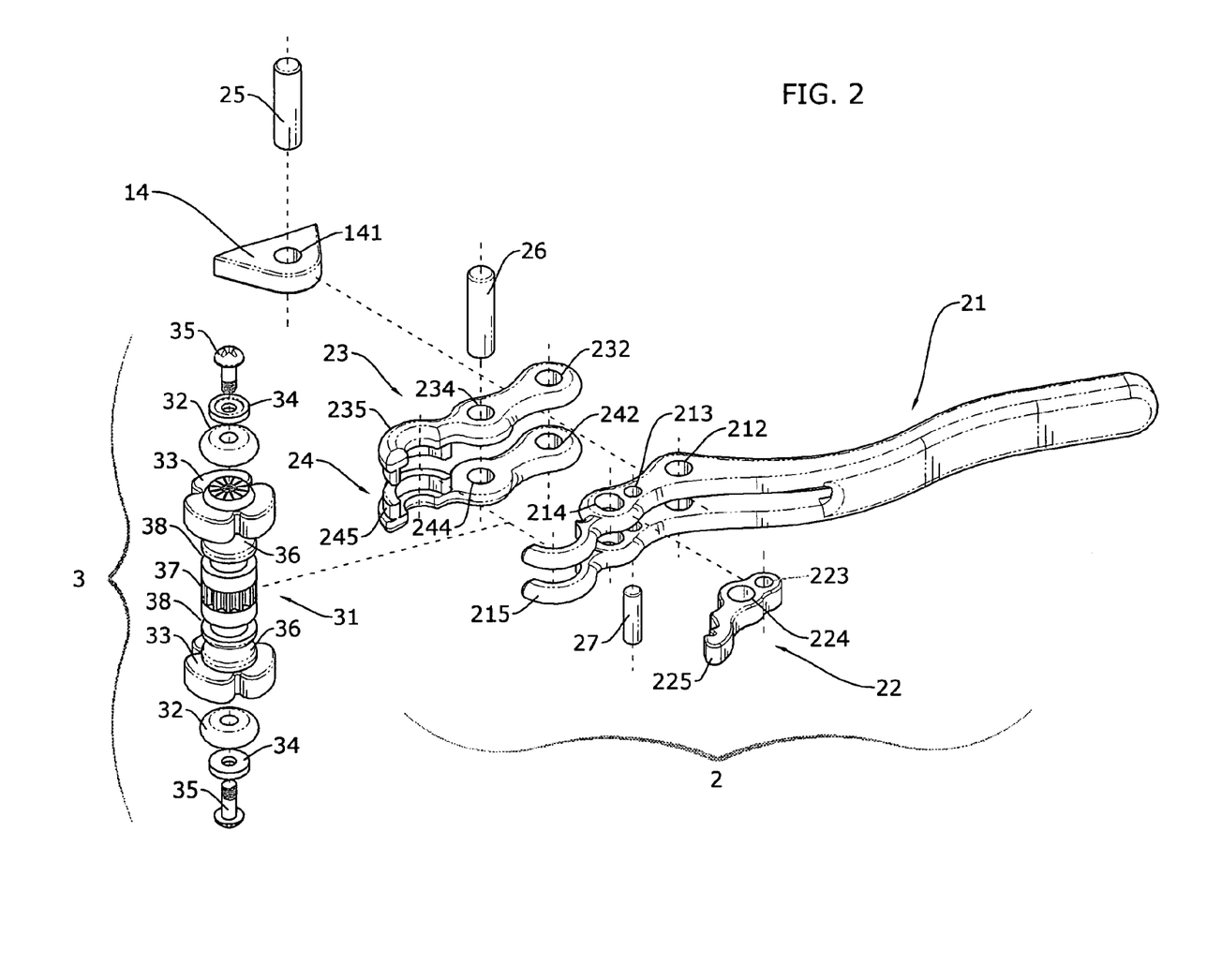
FIG. 2 is an exploded view of the rotor and the lever in the first embodiment of this invention.

Still referencing to FIG. 1, 3 and FIG. 4, also referencing to FIG. 2, the lever 2 comprises a lever body 21, interlock latch 22, interconnecting plates 23 and 24, pin 25 for attaching the lever body 21 to the triangular mount 14 of the handle body 1, pin 26 for the lever body 21 to connect the interconnecting plates 23, 24 and the interlock latch 22, and pin 27 for the lever body 21 to pull the interlock latch 22.

The lever body 21 is bifurcated on one end to facilitate pivotal installation on triangular mount 14, and to accommodate the interlock latch 22 being placed therein. At the distal end of the bifurcation, arcuate fingers 215 are shaped to hold the rotor. Bore 212 is inserted with pin 25 for the lever body to pivot on the handle body 1 through bore 141 on the triangular mount 14. Bore 213 is inserted with pin 27 to pull the interlock latch 22. Bore 214 is used to pull the interconnecting plate 23, 24 through pin 26. The shape of bore 214 is not truly circular but a curved slot, to permit a short lag for activating interlock mechanism.

The interlock latch 22 is pivoted on pin 26 through its bore 224, and pulled by pin 27 through its bore 223. Pawl 225 is shaped on one end of the interlock latch 22 engaged to lock the rotor 3 from rotation. The interconnecting plates 23 and 24 are in pair mainly to provide balanced transmission of pulling force from the lever body 21 to the rotor 3. Both plates are hinged on pin 25 through bore 232 and 242, and are pulled by pin 26 through bore 234 and 244. The arcuate fingers 235, 245 are used for pulling rotor 3, and together with fingers 215 on lever body 21, hold the rotor 3 rotatably in place.

The rotor body 31 at its middle is disposed with a circumferential interlock gear 37. On both side of the gear, grooved contour 38 is formed for purpose of keeping the rotor axially in position retained by fingers 235, 245. Further outwardly on both side, two reels 36 are formed and are in concave shape so that when wrapped around with floss, the laps of the floss will tend to fall in and overlap on each other to help tying down the floss. On both end of the rotor body 31, each has a trilobate knob 33 provided for user to turn the rotor to advance the floss. The lobulate grooves on the knobs provide passage of the floss from reel to clamp. The clamp is disposed on the outer side of the knob 33 formed by an elastomer ring 32, screw 35, washer 34 and knurled surface on the sidewall 331 of knob 33. The elastomer ring 32 is pressed down by screw 35 against the knurled surface of the sidewall 331 of the reel to form a clamp for tying down the free end of the floss. The inherent higher frictional coefficient of elastomer surface multiplied by the elastomer restoration pressure applied on the floss against the knurled surface will firmly grip the floss from loosening. To tie down the floss, the user can slide it into the slit formed between the elastomer ring and the knurled surface; to untie the floss, pulling it out of the slit will do.

To assemble the rotor-Lever mechanism, the interlock latch 22 is placed inside the bifurcated lever body 21 and inserted with pin 27 through bore 213 and 223 first. Then place the rotor on finger 215, and then place interconnecting plates 23 and 24 on top with fingers 235, 245 inserted in the grooves 38 of the rotor. Align the bore 214, 224, 234 and 244, then insert pin 26 through the bores, and finally heat weld or adhesive glue both end of pin 26 to the bore 234 and 244.

The rotor-lever mechanism can then be installed on the handle body with bore 212, 232, 242 aligned to the bore 141 on the triangular mount 14 and insert pin 25 through the bores, then heat weld or adhesive glue both end of pin 25 to the bore 232 and 242.

Figure 5:
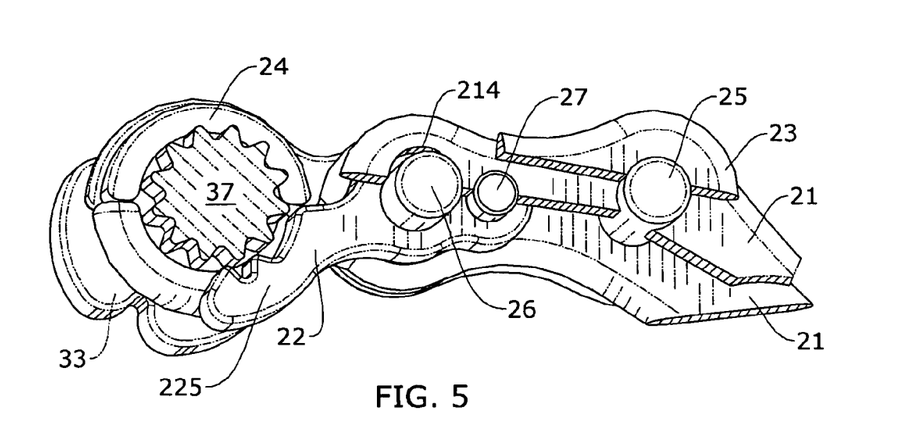
FIG. 5 is a partially cut away perspective view of the rotor-lever interlock mechanism, showing the lock is disengaged.
Figure 6:
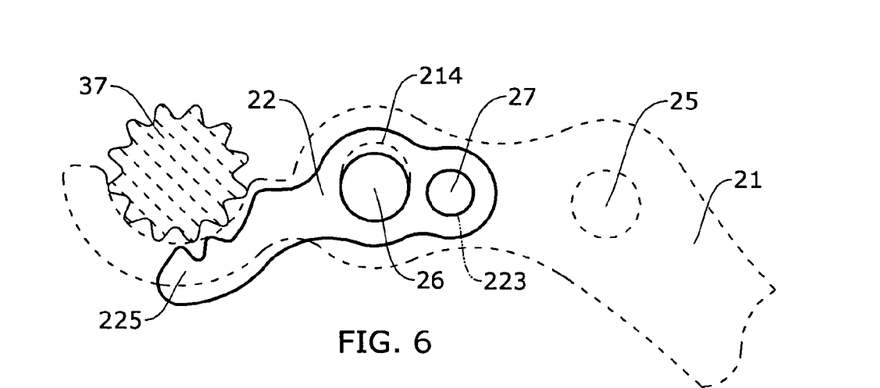
FIG. 6 is an illustrative sectional view of the rotor-lever interlock mechanism, showing the lock is disengaged.
Figure 7:
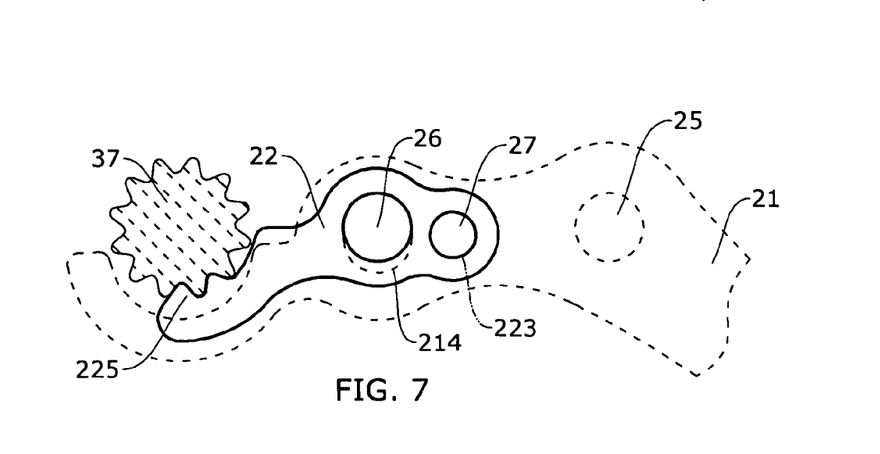
FIG. 7 is an illustrative sectional view of the rotor-lever interlock mechanism, showing the lock is engaged.

Referencing now to FIG. 5 to FIG. 7, the interlock mechanism is composed of lever body 21, interlock latch 22, interconnecting plates 23, 24, related pins 25, 26, 27, and the interlock gear 37 on the rotor. The interlock mechanism is devised to lock the rotor from rotation to prevent lateral shifting of the stretched floss when using sawing motion to slide it into interdental space, especially when encountering tightly adjoined teeth.

After the floss is threaded and wound ready for flossing, at the time the user presses the lever, the lever body 21 wilt first drive the interlock latch 22 to engage interlock gear 37, then press on the interconnecting plates 23, 24 which in turn press on the rotor 3 to lift the rotor away from the handle body 1 to stretch the floss. At the moment the lever body 21 starts to move, the floss winding on the reels on the rotor is holding the rotor in place, which in turn holding the interconnecting plates 23, 24 in place. Because the bore 214 is in a curved slot shape, pin 26 will not be affected at the beginning. Only after the upper rim of bore 214 is in contact with pin 26, the interconnecting plates 23, 24 will then be pressed, which in turn press on to the rotor. This short lag permits the pin 27 attached to lever body 21 to drive the interlock latch 22 pivoting on pin 26 to engage the pawl 225 into interlock gear 37. To accommodate different pivotal motions, i.e. pin 27 follows lever body 21 pivoting on the center of pin 25 but also pulls interlock latch 22 pivotally around the center of pin 26, the bore 223 is not in perfect round shape either. Clearance is opened on one side to give way of both pivotal motions in bore 223.

Reversely, by pressing the lever body 21 to push back the rotor 3 against the handle body 1, or hold the lever body 21 by hand pushing the rotor 3 toward the lever body 21 will disengage the latch. After freeing the rotor 3, advancing of the floss can then be entailed by turning the knob 33 on the rotor 3 to the desired direction.

FIG. 8 to FIG. 11 illustrate that the floss can be threaded through the tip of each arm, then threaded through the larger eyelet from bottom up to sit over the side of the handle body and directed to the reels, it then can be wound two laps on the reel prepared for collecting spent floss, six or more laps in the opposite circumferential direction on the reel prepared for supplying fresh floss, and then finally tied down both ends of it by the clamps. If 50 cm of floss is taken, there will be around 20 cm floss left hanging free on the supply side. The spent floss and fresh floss are separated through designated path, although relatively close when threading through the larger eyelet, the space therein provides ample separation as required for hygiene purpose. The floss is wound in opposite directions on two reels, when the rotor is turned by one of the knobs to the desired direction, one reel hauls in spent floss and the other pays off fresh floss. During flossing, frequent advancing of the floss is required. After a plural times of advancing with two or less laps left on the supplying reel, or the floss span becomes too slack beyond the lever's stretching range, the user can untie the floss from the clamp on the supplying reel and rewind six or more laps on said reel, then resume flossing.

Figures 8, 9:
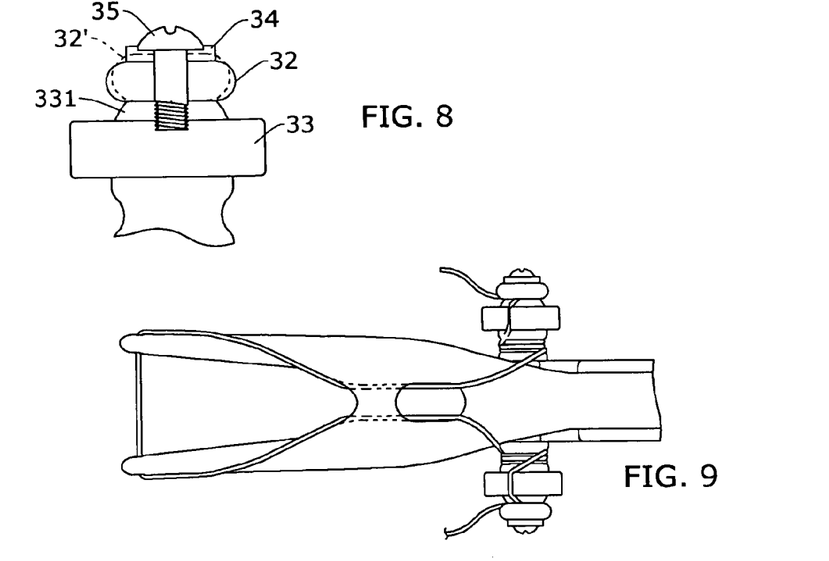
FIG. 8 is a sectional view of a clamp illustrating the elastomer ring before and after being pressed by a screw with washer against the sidewall of a reel.
FIG. 9 is a partial top view of a flossing tool showing the floss forms a loop by threading through arm tips and arms root eyelets then wound in opposite directions on two reels and finally tied down in the clamp slits.
Figure 10:
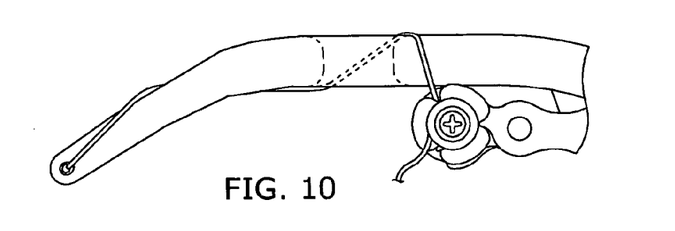
FIG. 10 is a partial side view of a flossing tool showing the floss forms a loop by threading through arm tips and arm root eyelets then wound and tied down.
Figure 11:
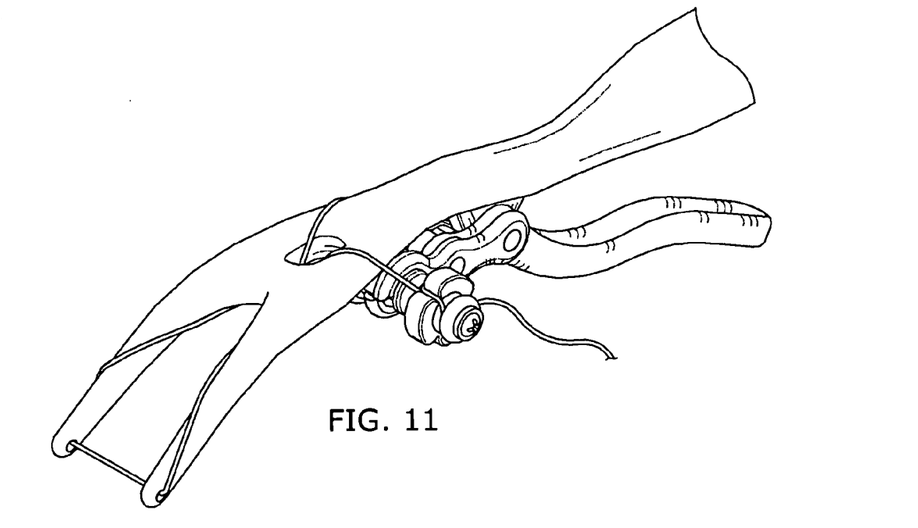
FIG. 11 is a partial perspective view of a flossing tool showing the floss loop is formed by threading through arm tips and arm root eyelets then wound and tied down.

The opposite direction winding fashion also serves to balance out the torque applied to both reels when the user press the lever to lift the rotor to stretch the floss, leaves the rotor rotatably stationary. Even when laps of the floss on two reels are so different result in significant difference of diameters, the less floss lapped reel will pull more force from the stretching floss to even out the torques.

To form a clamp, the elastomer ring 32 is pressed by screw 35 via washer 34 against knurled surface on the sidewall 331 of knob 33. Free end of the floss can be tied down by sliding into the slit formed between the elastomer ring 32 and sidewall 331. Wrapping one or more turns around the slit can further secure the floss if necessary. The dash line in FIG. 8 indicates the cross sectional view of the elastomer ring before pressed, designated as 32', in comparison to the ring after pressed. Being pressed, the elastic nature of the ring produces a constant restoration pressure against the knurled surface of the sidewall 331, thereby forms a clamp with a frictional grip. The shape of the sidewall is tapered, combining with the tubular surface of the elastomer ring provide easiness for floss to slide in.

Figure 12:
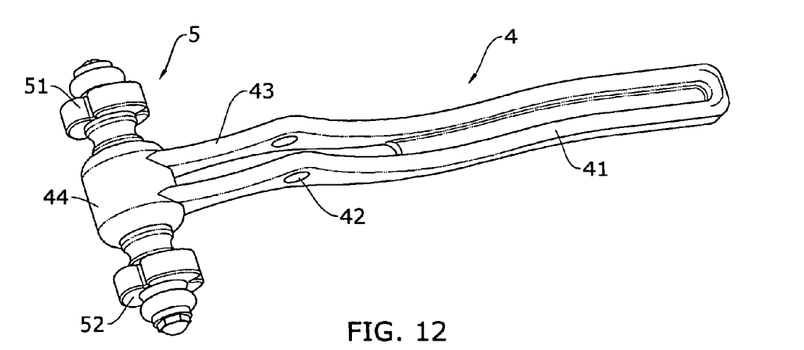
FIG. 12 is a perspective view of an alternative simplified rotor installed on an alternative simplified lever in the second embodiment of this invention.
Figure 13:
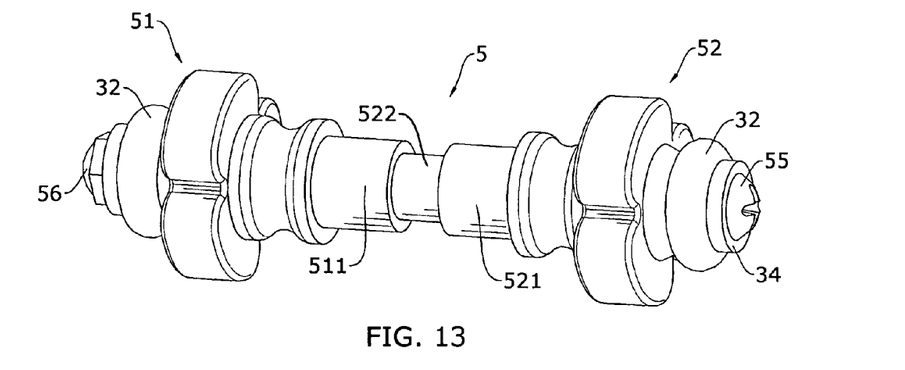
FIG. 13 is a perspective view of the rotor in the second embodiment of this invention.
Figure 14:
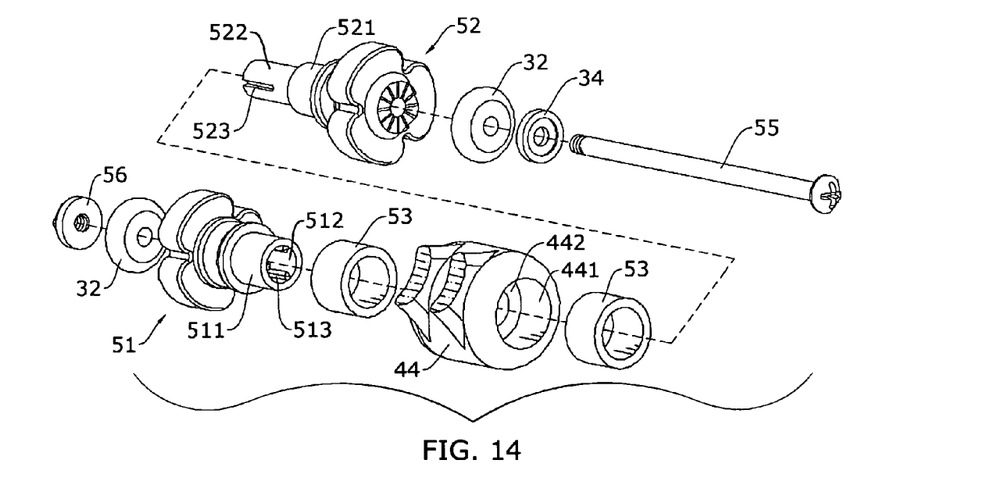
FIG. 14 is an exploded view of the rotor with part of the drum shape housing in position in the second embodiment of this invention.
Figure 15:
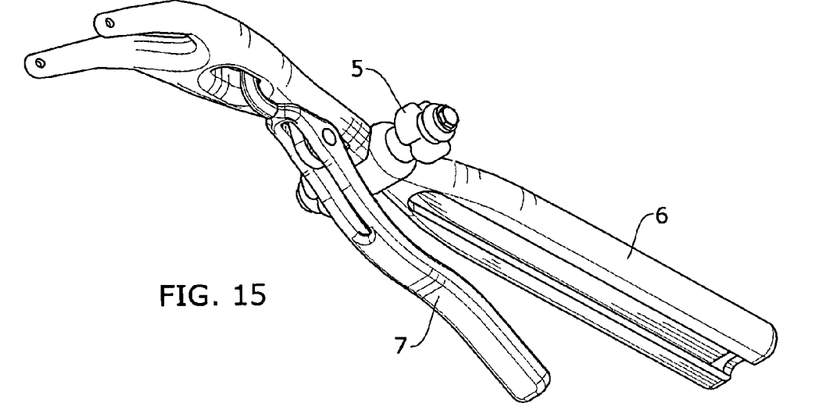
FIG. 15 is a perspective view of a flossing tool in the third embodiment of this invention, showing the lever at its initial position.
Figure 16:
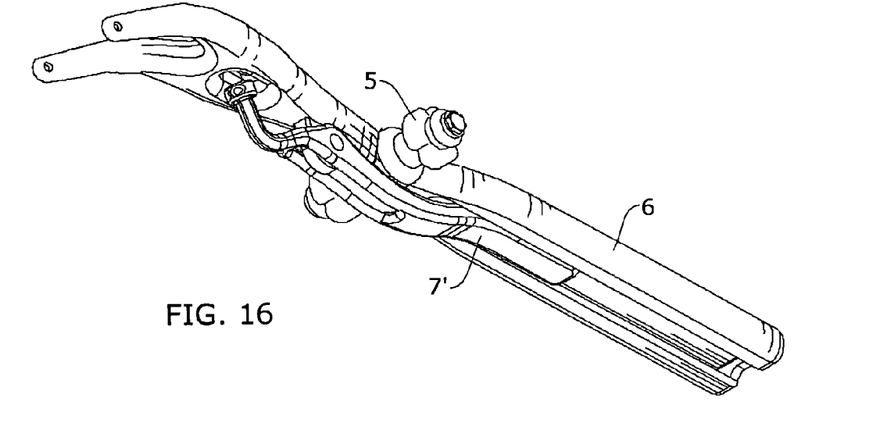
FIG. 16 is a perspective view of a flossing tool in the third embodiment of this invention, showing the lever at its fully pressed position.

Referencing to FIG. 12 to FIG. 14, a second embodiment of alternative lever and rotor is illustrated. The lever 2 and rotor 3 in the first embodiment can be substituted with a simplified lever 4 and a rotor 5. The lever 4 is different from the lever 2 only at the bifurcated end 43 where a drum shape housing 44 is formed to rotatably hold the rotor 5 therein.

The drum shape housing 44 is bored with two different diameters. A smaller diameter is bored on the middle partition 442 which retains the rotor axially stationary. Outer ends of the housing are bored with a larger diameter to form bearing seats 441 on both side of the partition 442.

For the rotor 5 to be rotatably installed and hold by the drum shape housing 44, the rotor can be separated in two halves. One half 51 has a socket 512 and in it three keys 513 are formed. Another half 52 has a connecting shaft 522 with three grooves 523 opened on the distal end. The halves are inserted from both side of the housing 44 into bearing seats 441 with the connecting shaft 522 further inserting through the partition 442 mating with socket 512 as well as the grooves 523 mating with keys 513, then bolted together with elastomer clamp rings 32 by a longer screw 55 with washer 34 and nut 56. The shaft journal 511 of rotor half 51 and the shaft journal 521 of rotor half 52 will be seated in the bearing seat 441, separated and axially retained by the partition 442. However the diameter of the bearing seat 441 is sizably larger than the diameter of journal shaft 511 and 521 leaves room for placing elastomer sleeves 53 in between. Purpose of this is to provide enough friction to resist the rotor from rotation when using sawing motion to slide the floss into interdental space similar to the function of interlock mechanism in the first embodiment. The outer diameter and thickness of the sleeves are made is such a way to provide a slight clearance to allow the rotor to rotate freely in the housing when there is no outside pressure in presence. But when the user lifts the rotor to stretch the floss, the rotor will be pulled and pressing its shaft journal 511 and 521 against the bearing seats 441 buffered by elastomer sleeves 53. The elastomer sleeves 53 will be deformed to fill in the clearance on the side of pulling force to create larger contact area on that side and with its inherent higher frictional coefficient, the frictional force will be enhanced as desired to resist the rotor from rotation, thereby resist the floss from lateral shifting especially when encountering tightly adjoined teeth. In flossing operation, therefore, disengaging the rotor prior to advancing of the floss is no longer needed. Other than that, the rest operation of the flossing tool illustrated in this second embodiment is very much the same as the flossing tool illustrated in the first embodiment.

Referring to FIG. 15 to FIG. 20, a third embodiment of the flossing tool is introduced. The handle body 6 is basically the same as the handle body 1 illustrated in the first embodiments, i.e. hallow handle 61, slot opening 62, triangular mount 64, eyelet 65 and bifurcated arms 66 are in same configuration with those on the handle body 1, except on its neck 63 a housing 67 is formed as an integral part of the handle body 6 and is bored same as the drum shape housing 44 in the second embodiment. The lever 7 is modified from the lever 4 by taking out the drum shape housing 44 and substitute with a yoke 73 and lever head 74. The rotor 5 used here in the third embodiment is the same rotor 5 as used in the second embodiment.

Figure 19:
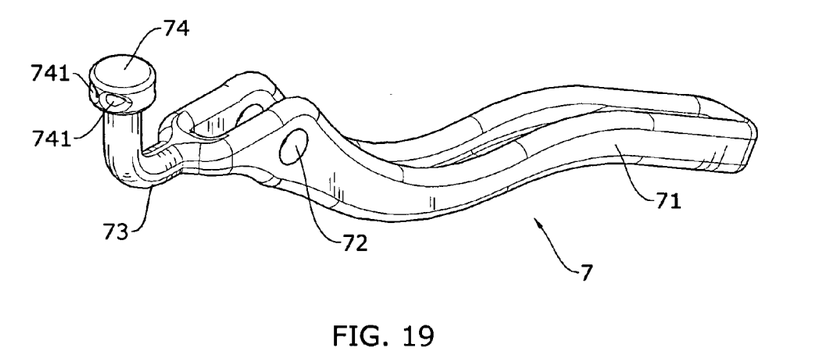
FIG. 19 is a perspective view of a lever for the third and fourth embodiment of this invention.

The yoke 73 closes up the bifurcated end of the lever body 71 and forms a lever head 74 at its angled distal end. The lever head 74 has two parallel longitudinally bored channels 741 for spent floss and fresh floss separately passing through. At its initial position, the lever head 74 is sticking up through the eyelet 65 exposing channels 741 above the top plan level of the handle body 6.

Figure 20:
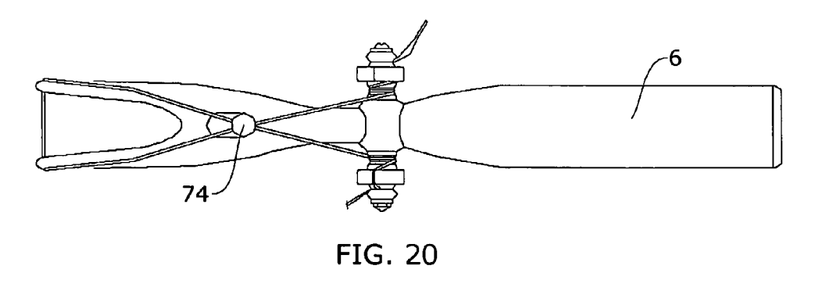
FIG. 20 is a top view of a flossing tool of the third embodiment, showing the floss is threaded through arm tips, lever head and reels on two sides of the rotor to form a loop.

To load the flossing tool in the third embodiment, around 50 cm floss can be taken with one end threaded through one of the channels, through eyelets on the arm tips, then back through the other channel, wound two laps on the reel for collecting spent floss and tied down, with the other end of floss wound six or more laps in opposite circumferential direction on the reel for supplying fresh floss, and finally tied down leaving around 25 cm of supplying floss hanging free on this side.

Figure 17:
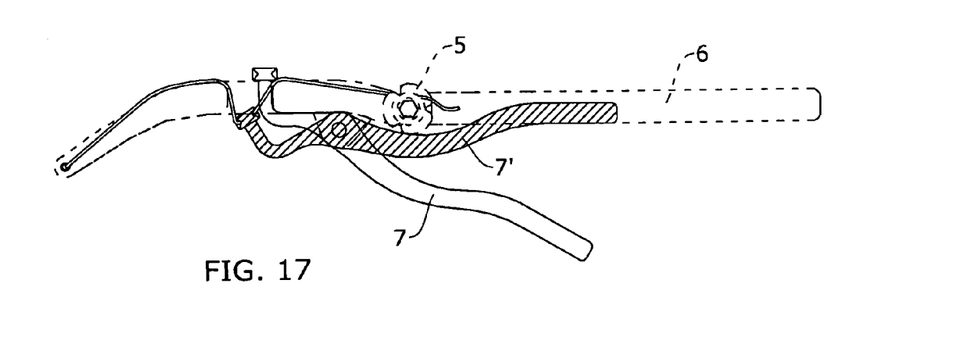
FIG. 17 is a partial sectional view illustrating the lever is fully pressed to stretch the floss, compare with the lever at its initial position, in the third embodiment of this invention.
Figure 18:
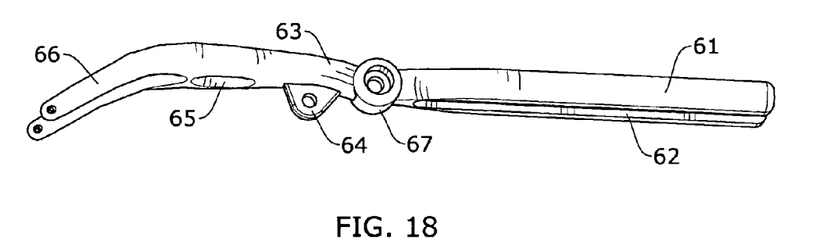
FIG. 18 is a perspective view of a handle body of the third embodiment showing the bore and partition for installing the rotor, and showing the triangular mount at the neck for pivotally installing a lever.

After loading, the flossing operation with the flossing tool in this third embodiment is much the same as the flossing tool in the second embodiment. By pressing the lever, the loop between arm tips and reels will be stretched; by turning the knob to desired direction, the floss will be advanced. For illustration, the lever 7 can be pressed to position 7' for tensioning operation as indicated in FIG. 17.

Referencing to FIG. 21 to FIG. 26, a fourth embodiment of a flossing tool is introduced. Said flossing tool includes an additional floss container 89 disposed at the end of the handle 81, also said flossing tool replaces previously introduced rotor 5 with an unidirectional rotor 9 and correspondingly the housing 67 with housing 87.

Figure 24:
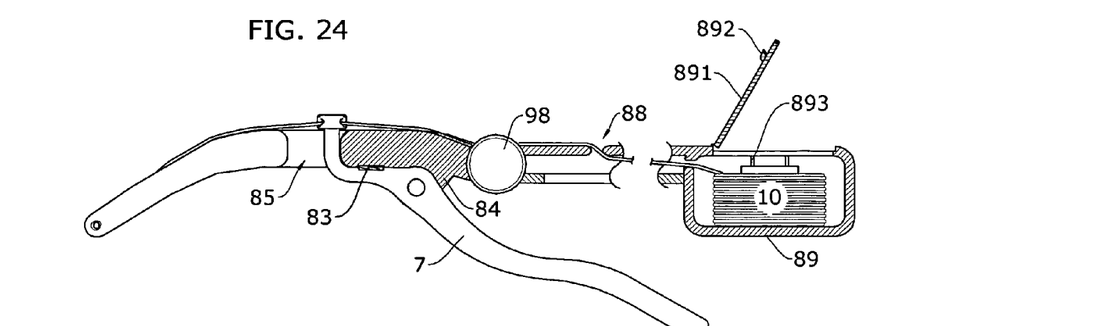
FIG. 24 is a partial sectional view of a flossing tool taken along the line 24-24 of FIG. 21, showing the floss is threaded from the floss spool through the passage holes, handle, clamp, lever head and arm tip.
Figures 25, 26:
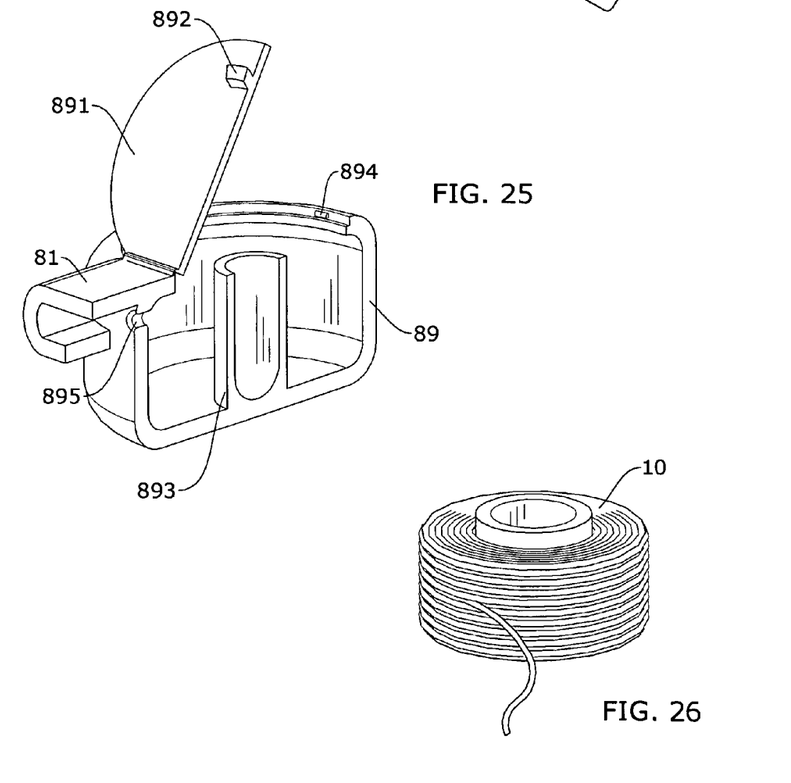
FIG. 25 is a perspective cutaway view of a floss container in the fourth embodiment of this invention.
FIG. 26 is a perspective view of an example of a floss spool that can be fitted in the floss container in the fourth embodiment of this invention.

The container 89 can be fitted with a floss spool 10 which can be rotated on pole 893, wherefrom the floss can be led through a small hole 895, passing the hollow handle and led through another small hole 88, then wrap one or two turns in the manually operable clamp, and then the rest of the floss can be threaded similarly like the flossing tool in the third embodiment. After flossing the soiled floss can be cut off by the cutter 83 placed underneath the handle body 8 and sheltered by the yoke 73 of the lever 7.

The container 89 has a cover 891 hinged on one side of the opening. On the other side of the hinge a grip 892 is formed for opening the cover. A pair of knurls 894 are formed on the opening of the container 89 at the opposite side of the hinge, with corresponding notches (not shown) to press fit and hold the cover closed.

Figure 23:
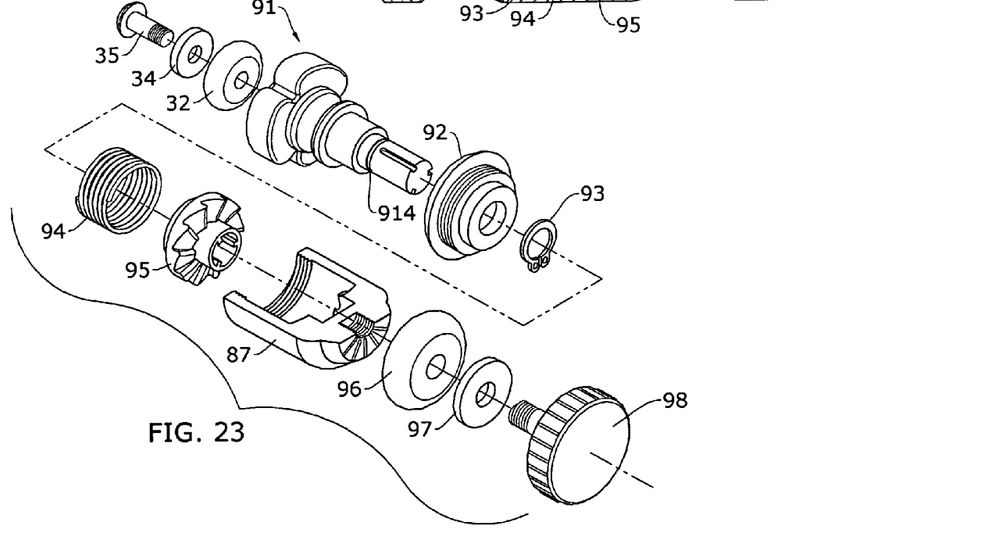
FIG. 23 is an exploded view of the rotor, ratchet mechanism, a part of the housing, and floss clamps in the fourth embodiment of this invention.

The rotor body 91 is in general same as the rotor half 52 except a circumferential groove 914 is made for clamping on retaining ring 93, and length of the connecting shaft and the three grooves on it is modified to fit in a ratchet mechanism. Same screw 35, washer 34 and elastomer ring 32 are used as in other embodiments to form a floss end clamp on the knob sidewall. The three grooves can mate with three keys in the bore of a ratchet gear 95. After inserting the rotor body 91 through the housing cap 92, clamping on the retainer ring 93 on the groove 914, then putting on spring 94 and sliding the ratchet gear 95 on the rotor connecting shaft, the housing cap 92 can then be screwed in the housing 87 to complete integration of the unidirectional rotor 9 and its housing 87.

The ratchet gear 95 slides along the rotor connecting shaft axially but rotates synchronously with the rotor by three keys formed inside its bore mating with the three grooves on the rotor connecting shaft. Facing opposite to the ratchet gear 95, a mating ratchet contour is molded on the bottom of the housing 87 to work in conjunction with the ratchet gear 95 under spring pressure to limit the rotor rotates only to the direction of reeling in spent floss.

Figures 21, 22:
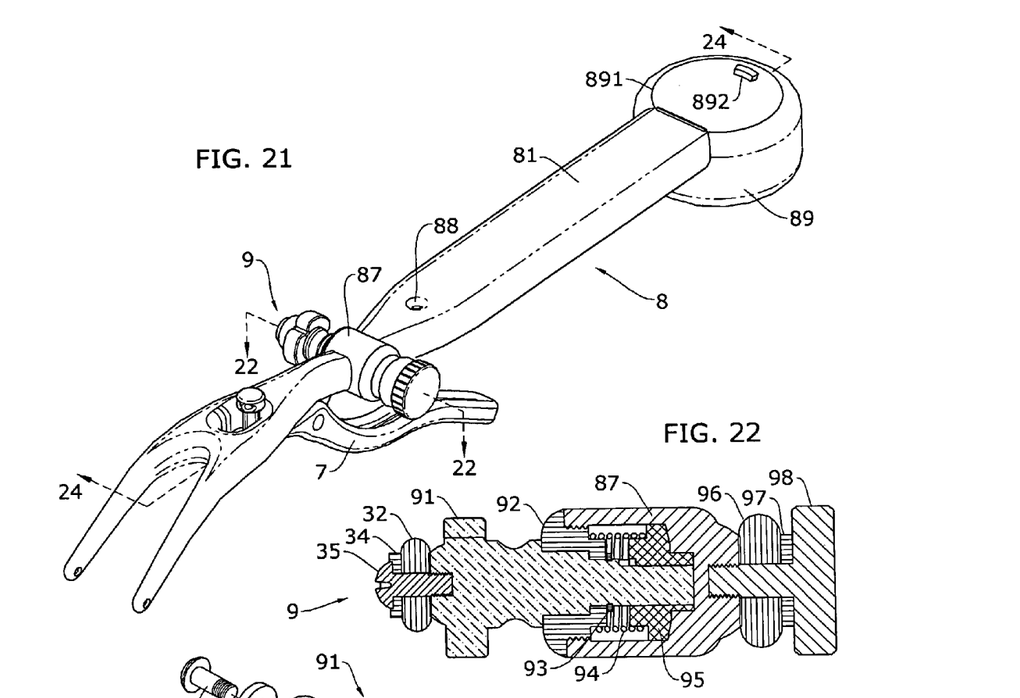
FIG. 21 is a perspective view of a flossing tool in the fourth embodiment of this invention.
FIG. 22 is a sectional view of the ratcheted rotor and floss clamps taken along the line 22-22 of FIG. 21.

A larger screw with a knob shape screw head 98 is disposed together with a larger washer 97 and a larger elastomer ring 96 to form a manually operable clamp. To prepare for flossing, the floss can be wrapped one or two turns in this clamp. When tied down by tightening the knob headed screw 98, the floss can be stretched taut by turning the rotor 91 alone. However, it is desirable that the floss only slightly stretched in advancing operation by turning the rotor, but leaves the tensioning control entirely to the lever. Because by operating the lever, the user can stretch the floss from taut to very taut, or slack it to its initial status, all at the will of the user. As a matter of fact, the unidirectional rotor 9 and its corresponding housing 87 can be replaced with rotor 5 and housing 67 excluding the supply reel floss clamp which should be manually operable and preferably be placed on the handle body.

Whereas the present invention has been described in relation to the drawings attached hereto as preferred examples, it is understood that other and further modifications, apart from those shown or suggested herein, may be made within the spirit and scope of the appended claims of the present invention.

What is claimed is:

1. A floss threading method applied on a flossing tool, whereon floss is threaded through tips of a pair of bifurcated arms and wound on two reels of a rotor to form a loop; floss winding on the reels are in opposite circumferential directions, one reel for hauling in spent floss and another for supplying fresh floss; advancing of the floss can be achieved by turning said rotor to the desired direction; stretching of the floss can be made either by lifting said rotor with a lever to increase the length of said loop, or by pulling a section of said loop with a lever for such lengthening; said opposite direction winding method results in said two reels with balanced torques during floss stretching operation leaving said rotor rotatably stationary.

2. A flossing tool with tensioning and advancing control comprising:
   a). a fork shape handle body having an elongated hollow handle on one end, a bifurcated pair of arms on the other, a triangular mount for pivotally installing a lever near the middle, and a housing near said triangular mount for holding a rotor; said arms each at its tip has one eyelet for floss threading through and together span a section for flossing, said arms at their root a larger eyelet is opened for a lever head to pass though;
   b). a rotor having two reels and two clamps for winding and tying down the floss respectively; and
   c). a lever pivoting on said handle body with one end forming a yoke with a head which can be swung through abovementioned larger eyelet reaching to a top side of said handle body; said head is bored with two parallel longitudinal channels for floss threading through to intervene a floss loop threaded between abovementioned arm tip eyelets and rotor reels; stretching or slacking of the floss can be maneuvered by pressing or releasing said lever.

\* \* \* \* \*

UNITED STATES PATENT AND TRADEMARK OFFICE
CERTIFICATE OF CORRECTION

PATENT NO. : 7,637,267 B2 Page 1 of 1
APPLICATION NO. : 11/498060
DATED : December 29, 2009
INVENTOR(S) : Jih Chang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 357 days.

Signed and Sealed this

Twenty-first Day of December, 2010

David J. Kappos
*Director of the United States Patent and Trademark Office*